United States Patent
Zink et al.

(10) Patent No.: US 9,699,361 B2
(45) Date of Patent: Jul. 4, 2017

(54) CAMERA SKID TRACTOR NOZZLE ASSEMBLY

(71) Applicant: STONEAGE, INC., Durango, CO (US)

(72) Inventors: Gerald Zink, Durango, CO (US); Rawlin Brown, Cortez, CO (US)

(73) Assignee: STONEAGE, INC., Durango, CO (US)

( * ) Notice: Subject to any disclaimer, the term of this patent is extended or adjusted under 35 U.S.C. 154(b) by 0 days.

(21) Appl. No.: 15/260,169

(22) Filed: Sep. 8, 2016

(65) Prior Publication Data

US 2016/0381258 A1    Dec. 29, 2016

Related U.S. Application Data (62) Division of application No. 14/212,531, filed on Mar. 14, 2014.

(60) Provisional application No. 61/804,639, filed on Mar. 23, 2013, provisional application No. 61/912,458, filed on Dec. 5, 2013.

(51) Int. Cl.
    *G01N 21/954*      (2006.01)
    *H04N 5/225*      (2006.01)

(52) U.S. Cl.
    CPC .......... *H04N 5/2252* (2013.01); *G01N 21/954* (2013.01)

(58) Field of Classification Search
None
See application file for complete search history.

(56) References Cited

U.S. PATENT DOCUMENTS

| | | | |
|---|---|---|---|
| 4,372,658 A | 2/1983 | O'Connor et al. |
| 4,567,514 A | 1/1986 | Morgan et al. |
| 5,964,414 A | 10/1999 | Hardy et al. |
| 5,992,247 A | 11/1999 | Manestar |
| 8,667,987 B2 | 3/2014 | Zink |
| 2004/0020270 A1 | 2/2004 | Kuikka |
| 2005/0275725 A1 | 12/2005 | Olsson et al. |
| 2012/0205405 A1 | 8/2012 | Zink et al. |

FOREIGN PATENT DOCUMENTS

| | | |
|---|---|---|
| CH | 672539 | 11/1989 |
| WO | WO 2006/127095 | 11/2006 |

*Primary Examiner* — Robert R Raevis
(74) *Attorney, Agent, or Firm* — Greenberg Traurig, LLP (57) ABSTRACT

A camera skid and thrust nozzle assembly for supporting a camera while being positioned in a tubular pipe or conduit spaced from any wall of the conduit and permitting movement of the assembly along the conduit. The assembly includes a cage rotatably fastened to a high pressure fluid tractor nozzle, wherein the cage can rotate about an axis through the tractor nozzle. A camera support structure is fastened within the cage for rotation of the support structure about the axis independent of rotation of the cage. The camera support structure has a weight attached thereto for urging rotational orientation of the camera support structure within the cage according to a sensed external gravitational force on the assembly.

15 Claims, 6 Drawing Sheets

CAMERA SKID TRACTOR NOZZLE ASSEMBLY

CROSS REFERENCE TO RELATED APPLICATIONS

This application is a divisional of U.S. Non-provisional patent application Ser. No. 14/212,531, filed Mar. 14, 2014, which claims the benefit of priority of U.S. Provisional Application No. 61/804,639, filed Mar. 23, 2013, and No. 61/912,458, filed Dec. 5, 2013, both entitled Camera Skid Tractor Nozzle Assembly. These applications are incorporated herein by reference in their entirety.

BACKGROUND OF THE DISCLOSURE

A high pressure rotary nozzle and tractor device is disclosed in US Patent Application Publication No. 20120205405. A high pressure fluid switching valve tractor device for use with a nozzle is also disclosed in U.S. Pat. No. 8,667,987. These publications are hereby incorporated by reference in their entirety. Such nozzles and tractor devices are particularly well suited to industrial uses where the operating parameters can be in the range of 1,000 to 40,000 psi and flow rates of 5 to 150 gpm, and when rotary nozzles are employed, rotating speeds of 10 to 1000 rpm or more may be needed.

For inspection of sewer lines and other large buried or surface piping systems there is a need for a robust mechanism for viewing such systems internally to better understand blockages, restrictions and obstructions without unearthing and breaking open the system. Several solutions to this problem have been identified. One such system places a camera on a sled at the end of a hose that has jet nozzles to propel the sled down the piping ahead of the hose. However, the hose naturally has some twist as it is advanced and retracted which tends to cause the sled to tip over. Therefore there is a swivel that is installed to allow the hose to roll while the sled stays upright. However, friction in the swivel at operating pressure apparently prevents this swivel from performing the desired function. Thus the sled upon which the camera is mounted tips over and becomes submerged in whatever fluid is within the piping, especially when trying to negotiate around bends in the piping system. The present disclosure addresses this difficulty in a new manner.

SUMMARY OF THE DISCLOSURE

Embodiments in accordance with the present disclosure eliminate a fluid carrying swivel to address the above difficulty. One embodiment in accordance with the present disclosure includes a camera module mounted on a camera tray that is rotatably supported from journal bearings on an axle that extends through one end of a cage skid that is, in turn, fastened to a tractor nozzle that is attached to an end of a high pressure hose. Such a hose may be pressurized to somewhere between 100 psi to 20000 psi, depending on the service for which it is designed.

The cage skid is preferably made of a central bearing sleeve having three or more radially extending ribs that extend outward from the central bearing sleeve and bend so as to extend parallel to the central bearing sleeve to a point beyond the camera tray. These ribs then reconnect around the camera module so as to present a protective cage structure around the camera module. The three or more ribs are preferably axially symmetric, so that if the cage rotates on its axis, the camera module is held at an elevation above an anticipated liquid level in the conduit or pipe. This axle is rotatably supported by the skid and the same axle rotatably supports the camera tray such that it can freely rotate to remain upright as the cage rotates on its axis. The axle extends axially from a tractor nozzle that may have a plurality of rearwardly directed nozzle tips to provide a forward thrust on the skid so as to at least assist in propelling the skid through a length of pipe in a piping system such as a sewer line. A conventional high pressure hose is attached to the tractor nozzle.

Another embodiment could involve two skids positioned in parallel contacting the bottom of a pipe if the pipe is large enough. Such a configuration would greatly reduce the likelihood of tipping of the cage skids and thus improve assurance the camera module would not likely become submerged in fluid within bottom portion of a pipe through which it is being propelled by fluid jets.

Another embodiment of an assembly in accordance with the present disclosure includes a camera module mounted on a camera tray that is rotatably supported from an axle that extends through one end of a cage skid that is, in turn, fastened to a rotary bearing in turn mounted to a rotary nozzle and to a switcher tractor nozzle such as is disclosed in US Patent Publication No. 20120205405 mentioned above. This switcher tractor nozzle is then attached to an end of a high pressure hose. Such a hose may be pressurized to somewhere between 100 psi to 20000 psi, depending on the service for which it is designed. The cage skid is preferably made of a central bearing sleeve having three or more radially extending ribs that extend outward from the central bearing sleeve and bend so as to extend parallel to the central axial bearing sleeve to a point beyond the camera tray. These ribs then reconnect around the camera module so as to present a protective cage structure around the camera module. The skid rotatably supports the same axle as the camera tray such that it can freely rotate to negotiate piping bends. The axle extends axially from a tractor nozzle that may have a plurality of rearwardly directed nozzle tips to provide a forward thrust on the skid so as to at least assist in driving the skid through a length of pipe in a piping system such as a sewer line.

In both of these embodiments described above, the camera module is preferably mounted to a separate journal bearing sleeve on the common axle via a radially offset camera tray such that the centerline of the camera is parallel to the axle, but the entire center of gravity of the module and tray is displaced from the axle. In this way the gravitational force on the overall assembly will keep the camera module vertically aligned as the cage skid assembly is propelled along the piping. Similarly the cage skid is fastened to the common axle by another journal bearing sleeve so that the skid is free to rotate on the axle separately so as to readily negotiate bends and around obstacles in the piping segment in which it is inserted.

A third embodiment in accordance with the present disclosure is designed for large diameter piping systems such as those having a diameter greater than 18 inches. In this embodiment each of the three ribs is fitted with a frame extension that supports two spaced wheels. Thus the cage skid is supported on three frame extensions each having a set of wheels. The cage skid then rolls along the inside pipe wall. Each end of the frame extension may be quickly attached or detached from the skid rib via a couple of bolts that sandwich the rib therebetween.

A fourth embodiment in accordance with the present disclosure is designed for essentially small/moderate diameter piping systems within a range of between 4-10 inches. In this embodiment the skid cage takes the form of a unitary cylindrical can shaped housing having an open front portion, a tubular mid portion and a cup shaped rear portion. The camera is again mounted for rotation on a shaft within the housing.

DETAILED DESCRIPTION

Figure 1:
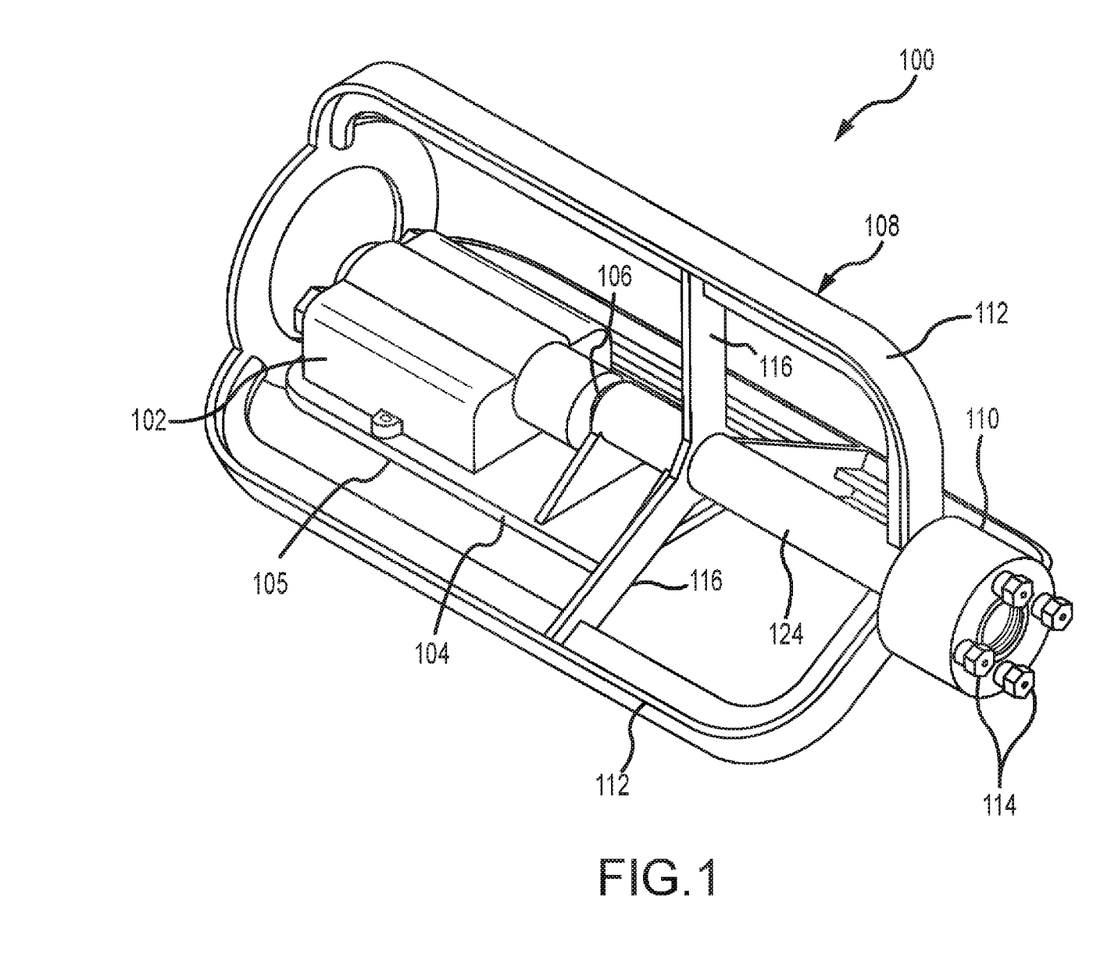
FIG. 1 is a composite of a side view, front and rear end views and several perspective views of a first embodiment of a camera skid assembly in accordance with this disclosure.

FIG. 1 includes several views of a first embodiment 100 in accordance with the present disclosure. Skid nozzle assembly 100 includes a camera module 102 mounted on a camera tray 104 that is rotatably supported from an axle 106 that extends through one end of a cage skid 108. The cage skid 108 is, in turn, fastened to a tractor nozzle 110 that is attached to an end of a high pressure hose (not shown). Such a hose may be pressurized to somewhere between 100 psi to 20000 psi, depending on the service for which it is designed. The cage skid 108 is preferably made of a central bearing sleeve having three or more radially extending ribs 112 that extend outward from the central bearing sleeve and bend so as to extend parallel to the central bearing sleeve to a point beyond the camera tray. These ribs 112 then reconnect around the camera module 102 so as to present a protective cage structure around the camera module 102. This axle 106 supports the cage 108 and also the camera tray 104. The axle 106 extends axially from a tractor nozzle 110 that may have a plurality of rearwardly directed nozzle tips 114 to provide a forward thrust on the skid 108 so as to at least assist in driving the skid through a length of pipe in a piping system such as a sewer line. The cage skid 108 also preferably has a set of three or more radial support struts 116 that extend outward to support the axially extending portions of the ribs 112.

Figure 2:
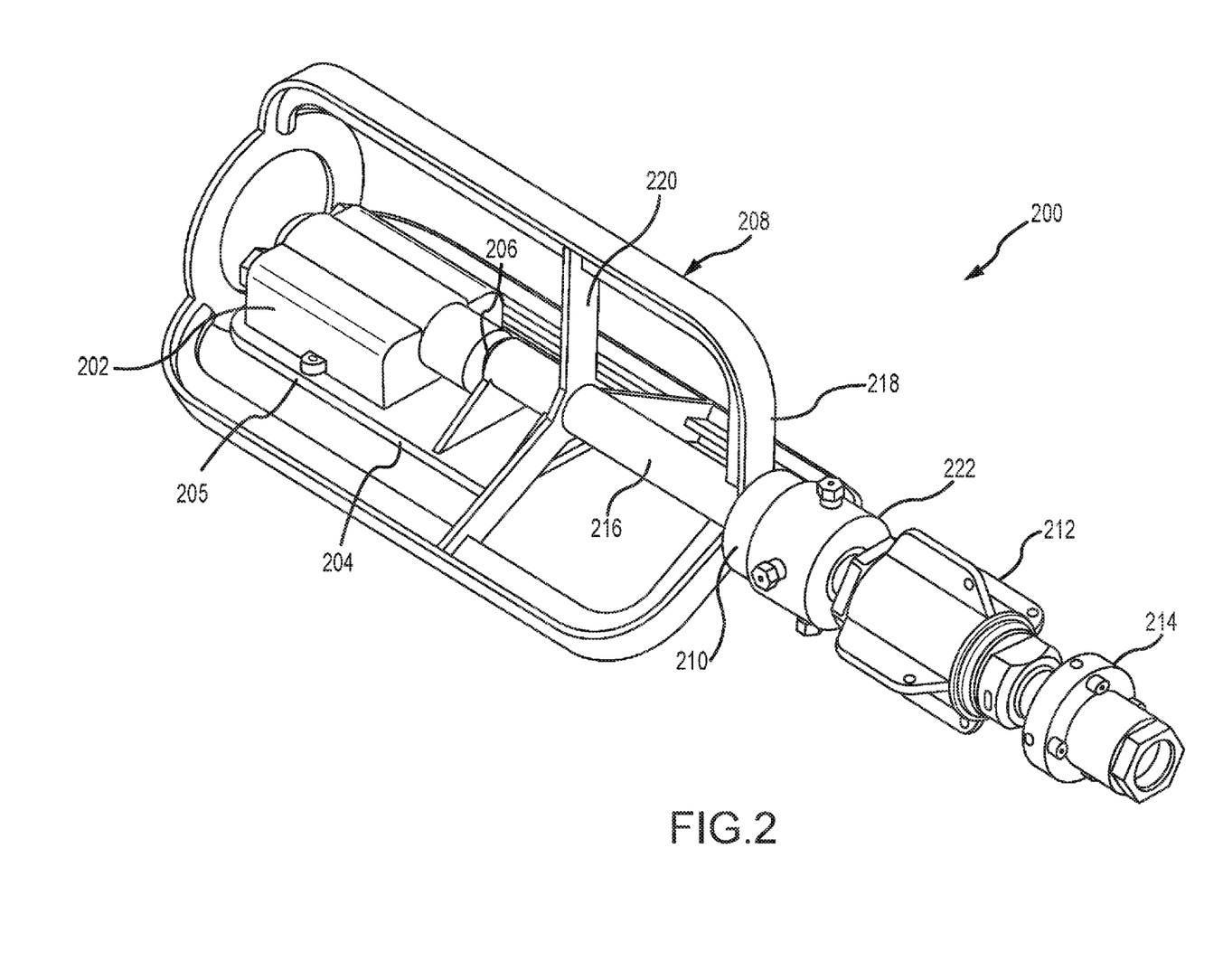
FIG. 2 is a composite of a side view, front and rear end views and several perspective views of a second embodiment of a camera skid nozzle assembly in accordance with this disclosure.

FIG. 2 shows a second embodiment of an assembly 200 in accordance with the present disclosure. Nozzle skid assembly 200 includes a camera module 202 mounted on a camera tray 204 that is rotatably supported from an axle 206 that extends through one end of a cage skid 208 that is, in turn, fastened to a rotary bearing 210 in turn mounted to a rotary nozzle 222 and to a switcher tractor nozzle 214 such as is disclosed in US Patent publication No. 20120205405 mentioned above. This switcher tractor nozzle 214 is then attached to an end of a high pressure hose (again, not shown). Such a hose may be pressurized to somewhere between 100 psi to 20000 psi, depending on the service for which it is designed. The cage skid 208 is preferably made of a central bearing sleeve 216 on the axle 206. The sleeve 216 also has three or more radially extending ribs 218 that extend outward from the central bearing sleeve 216 and bend so as to extend parallel to the central axial bearing sleeve 216 to a point beyond the camera tray 204. These ribs 218 then reconnect around the camera module 202 so as to present a protective cage structure around the camera module 202. This axle 206 rotatably supports the cage skid 208 and separately the camera tray 204 such that it can freely rotate. A set of three radial struts 220 each extends from the sleeve 216 to one of the ribs 218 to provide rigid support for the cage assembly 208. The axle 206 extends axially from a rotary bearing 210 that may optionally be in turn connected to a rotary cleaning jet nozzle 222 and another nozzle 212. This nozzle 212 is then connected to the switcher tractor nozzle 214 that includes both cleaning and a plurality of rearwardly directed nozzle jet tips to provide a forward thrust on the skid so as to at least assist in driving the skid through a length of pipe in a piping system such as a sewer line.

In both of these embodiments described above, the camera module 102, 202 is preferably mounted to a separate journal bearing sleeve on the common axle 106, 206 via a radially offset camera tray 104, 204 such that the centerline of the camera is parallel to the axis of the axle 106, 206, but the entire center of gravity of the module and tray is displaced from the axle. In this way the gravitational force on the overall assembly will keep the camera module vertically aligned as the cage skid assembly is propelled along the piping. A weight 105, 205 may be incorporated into each of the camera trays 104, 204 to ensure that the center of gravity is displaced from the axle 106, 206. Similarly the cage skid 108, 208 is fastened to the common axle 106, 206 by another journal bearing sleeve 124, 216 so that the skid 108, 208 is free to rotate separately on the axle 106, 206 so as to readily negotiate bends and around obstacles in the piping segment in which it is inserted.

Figure 3:
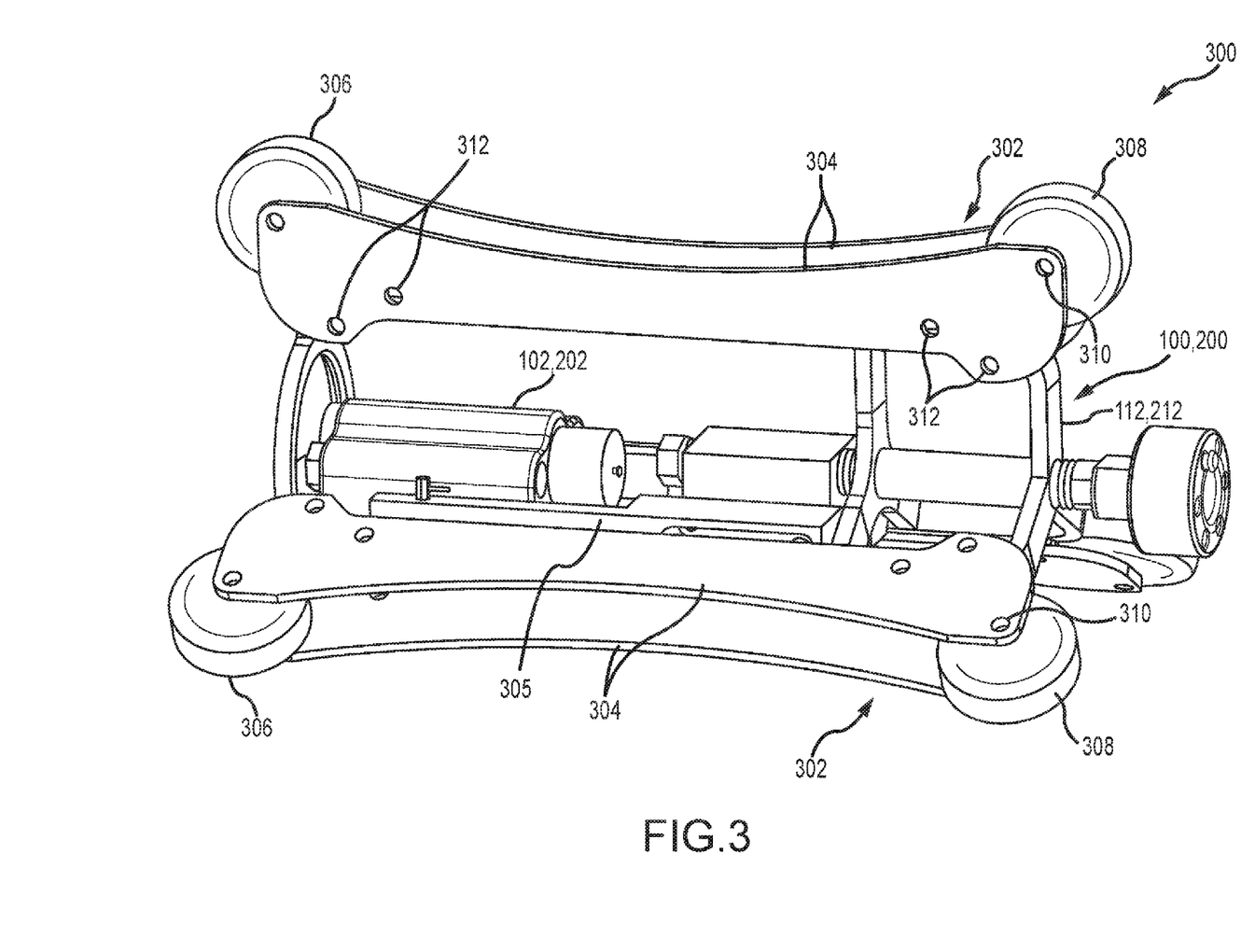
FIG. 3 is a perspective view of an assembled skid as shown in either FIG. 1 or 2 with wheeled extensions on each of the skid ribs.

A further embodiment of the camera skid assembly in accordance with the present disclosure is shown in a perspective view in FIG. 3. This skid assembly 300 incorporates a skid assembly as described above with reference to FIG. 1 or 2 for use in large diameter piping systems, such as for deploying the skids 100 and 200 in pipes greater than about 18 inches in diameter.

Skid assembly 300 includes one of skids 100 or 200, a weight 305 attached to the camera tray 104, 204, and a set of three wheeled frame extension assemblies 302. Each frame extension assembly includes a pair of elongated side plates 304, a front wheel 306 and a rear wheel 308. The pair of side plates 304 are fastened to and sandwich therebetween one of the ribs 112, 212. The side plates 304 also sandwich and support axles 310 for the wheels 306 and 308.

Each of the extension assemblies 302 is clamped to its rib 112, 212 via two bolt holes 312 and pairs of bolts and nuts (not shown). One of each pair of bolts in the holes 312 is threaded through the interior space of the rib 112, 212 and the other outside the rib 112, 212 so as to capture the rib 112, 212 between the side plates 304 and each pair of bolts. This clamping technique is exemplary. Other fastening techniques may be utilized, that are known, to secure each of the extension assemblies 302 to the skid 100, 200.

Figure 4:
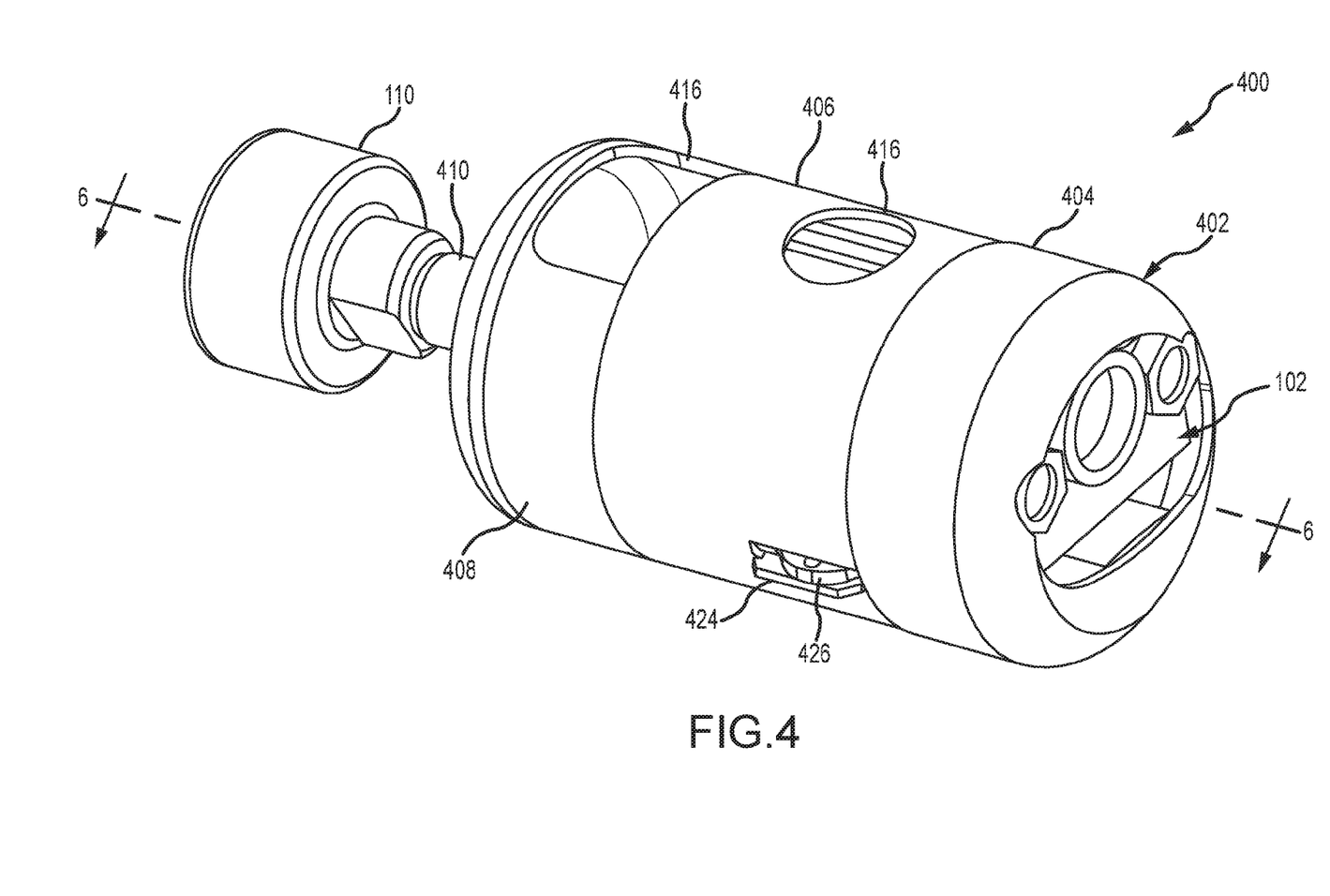
FIG. 4 is a perspective view of a further camera skid assembly for use in small to moderate pipe diameter systems.
Figure 5:
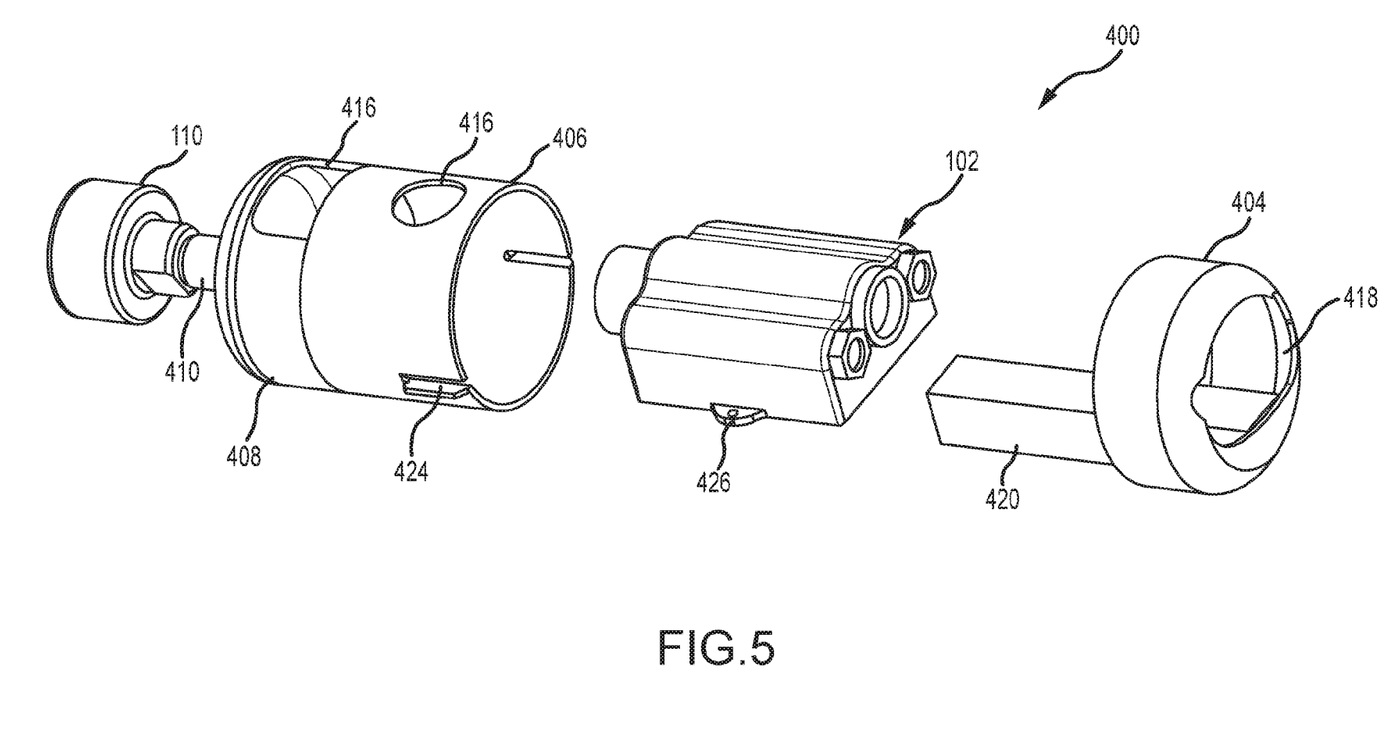
FIG. 5 is an exploded perspective view of the assembly shown in FIG. 4.
Figure 6:
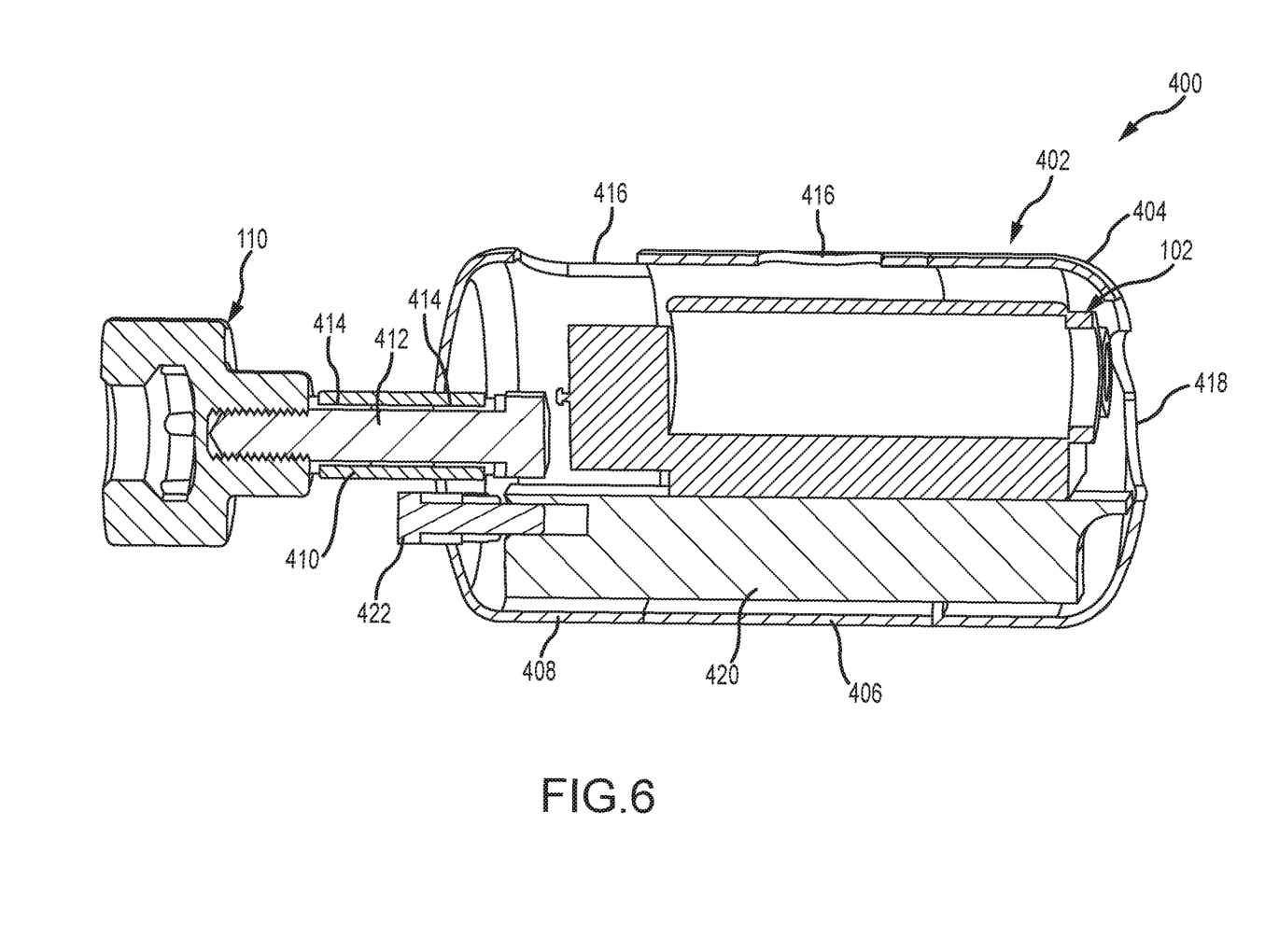
FIG. 6 is a longitudinal sectional view of the assembly of FIGS. 4 and 5 taken along the line 6-6 in FIG. 4.

A fourth embodiment of a camera skid assembly 400 is shown in FIGS. 4-6. This assembly 400 is similar to those assemblies 100 and 200 in that all carry a rotatably mounted camera assembly 102. In this embodiment 400, however, the cage 402 is of reduced size such that the assembly can be utilized in piping/conduit systems having a diameter between, for example, 4-10 inches. In this embodiment, the cage 402 is essentially a hollow can structure having a cup shaped open front cage portion 404, a straight tubular mid portion 406, and a cup shaped rear cage portion 408. An axially centered tubular bearing sleeve 410 is fixed to and extends rearward from the rear cage portion 408. Bearing sleeve 410 may be welded in place on the rear cage portion 408 or otherwise fastened thereto.

The rear cage portion 408 is rotatably fastened to a tractor nozzle 110 via the bearing sleeve 410 and an axle bolt 412 that extends through a pair of bushing bearings 414 in the bearing sleeve 410. The axle bolt 412 is threaded into the head end of the tractor nozzle 110. Operation of the tractor nozzle 110 is as previously described above.

Preferably the mid cage portion 406 is welded to or otherwise fastened to the rear cage portion 408 prior to assembly of the camera module into the rear cage portion 408. The rear cage portion 408 and the mid cage portion 406 each preferably has at least one opening 416 to permit access to camera module controls.

The head or front cage portion is a hollow cup shaped solid body that has a central opening through which the camera can see down the piping system into which the assembly is inserted. Fixed to an interior surface of the front cage portion 404 is a generally rectangular weight block 420. This weight block 420 provides the mass to keep the camera assembly 102 and the cage 402 properly aligned due to gravity as the skid 400 is pushed by the tractor nozzle 110 along a pipe in which it is deployed.

The camera assembly 102 is removably fastened to the mid cage portion 406 so as to rotate with the cage 402. The mid cage portion 406 has a pair of diametrically opposed slotted flanges 424. The camera assembly 102 has opposing flanges 426 which slide into and onto the flanges 424 as is shown in the assembled view of FIG. 4. In this way the camera assembly 102 is sandwiched between the mid cage portion 406 and the front cage portion 404. During assembly, first the rear cage portion 408, with mid cage portion fixed thereto, is assembled via the axle bolt 412 to the tractor nozzle 110. Then the camera assembly 102 is slipped into the mid cage portion 406 such that the flanges 424 and 426 overlappingly engage and the weight block 420 slides beneath the camera assembly 102. Finally, the front cage portion 404 is fitted to the rear and mid cage portions 406 and 408 so that a capture bolt 422 aligns with a threaded recess in the weight block 420. The capture bolt 422 carried by the rear cage portion 408 is then threaded into the weight block 420 to draw the cage portions 408 and 404 together to complete the assembly.

When fully assembled, the cage 402 can rotate freely about the bearing axle 412. When held horizontal as is shown in FIG. 6, gravity will locate the weight block 420 downward thus properly orienting the camera 102 within the cage assembly 402. In this embodiment the weight block 420 orients both the camera 102 and the cage 402 itself together in order to produce an erect image from the camera assembly 102. Preferably the flanges 424 and 426 are sized such that they do not protrude substantially beyond the side wall of the tubular mid cage portion 406 so that interference with proper orientation of the assembly 400 and snagging is minimized during deployment.

Alternatively a combination of a switching valve such as disclosed in U.S. Pat. No. 8,667,987 could be connected in tandem with a rotary cleaning nozzle 212, and nozzle 212 may include a rotational speed limiting device such as a viscous damper as disclosed in U.S. Pat. No. 5,964,414 in order to maintain nozzle rotational speeds within a desired range. Other configurations could also be used. For example, rotary bearings 210 may be incorporated between the tandem components, and additional tractor nozzles may be incorporated into the component string of the assembly other than is specifically described and shown in the accompanying figures as may be needed for an encountered piping system being explored.

All such changes, alternatives and equivalents in accordance with the features and benefits described herein, are within the scope of the present disclosure. Such changes and alternatives may be introduced without departing from the spirit and broad scope of my invention as defined by the claims below and their equivalents.

What is claimed is:

1. A camera skid and thrust nozzle assembly comprising:
   a tractor nozzle;
   a cage rotatably fastened to and ahead of the tractor nozzle, wherein the cage can rotate about an axis through the tractor nozzle; and
   a camera support structure fastened within the cage for rotation of the support structure about the axis independent of cage rotation, the support structure configured to carry a camera in front of the tractor nozzle oriented to view ahead along the axis, wherein the support structure includes a weight for urging rotational orientation of the camera support structure about the axis according to a sensed external gravitational force.

2. A camera skid and thrust nozzle assembly for supporting a camera in a tubular pipe or conduit spaced from any wall of the conduit for movement of the assembly along the conduit, the assembly comprising:
   a cage rotatably fastened to a tractor nozzle, wherein the cage can rotate about an axis through the tractor nozzle; and
   a camera support structure configured to carry a camera in front of the tractor nozzle oriented to view ahead along the conduit fastened within the cage for rotation of the support structure about the axis independent of rotation of the cage, the camera support structure having a weight attached thereto for urging rotational orientation of the camera support structure within the cage according to a sensed external gravitational force on the assembly.

3. The assembly according to claim 2 wherein the cage has plurality of ribs spaced around the camera support structure, each rib having a portion extending parallel to the axis.

4. The assembly according to claim 3 wherein the cage has an odd number of ribs.

5. The assembly according to claim 2 wherein the camera support structure and the cage are each independently rotatably supported on an axle supported from the tractor nozzle.

6. The assembly according to claim 5 wherein each of the ribs has a radial portion spacing the camera support structure from the rib portion extending parallel to the axis.

7. The assembly according to claim 6 further comprising a wheeled frame extension fastened to each of the plurality of ribs.

8. The assembly according to claim 7 wherein the wheeled frame extension comprises:
   at least one elongated plate fastened to one of the ribs, the plate supporting one or more wheels for rolling along an inside wall of the pipe or conduit.

9. The assembly according to claim 7 wherein the frame extension comprises a pair of elongated plates sandwiching the rib, the pair of elongated plates supporting therebetween a front wheel and a rear wheel aligned parallel to the axially extending portion of the rib.

10. A camera skid and thrust nozzle assembly for supporting a camera in a tubular pipe or conduit spaced from any wall of the conduit for movement of the assembly along the conduit, the assembly comprising:

a cage rotatably fastened to and in front of a tractor nozzle, wherein the cage can rotate about an axis through the tractor nozzle;

a camera support structure fastened within the cage for rotation of the support structure about the axis independent of rotation of the cage, the camera support structure configured to carry a camera in front of the tractor nozzle oriented to view ahead along the conduit and having a weight attached thereto for urging rotational orientation of the camera support structure within the cage according to a sensed external gravitational force on the assembly; and a wheeled frame fastened to the cage.

11. The assembly according to claim 10 wherein the cage includes plurality of ribs spaced around the camera support structure, each rib having a portion extending parallel to the axis.

12. The assembly according to claim 11 wherein the wheeled frame includes a pair of elongated plates sandwiching each rib, the pair of elongated plates supporting therebetween a front wheel and a rear wheel aligned parallel to the axially extending portion of the rib.

13. The assembly according to claim 10 wherein the cage has an odd number of ribs.

14. The assembly according to claim 13 wherein each of the ribs has a radial portion spacing the camera support structure from the rib portion extending parallel to the axis.

15. The assembly according to claim 10 wherein the camera support structure and the cage are each independently rotatably supported on an axle supported from the tractor nozzle.

* * * * *

UNITED STATES PATENT AND TRADEMARK OFFICE
CERTIFICATE OF CORRECTION

PATENT NO. : 9,699,361 B2
APPLICATION NO. : 15/260169
DATED : July 4, 2017
INVENTOR(S) : Zink et al.

Page 1 of 1

It is certified that error appears in the above-identified patent and that said Letters Patent is hereby corrected as shown below:

In the Specification

In Column 4, Line 51, delete "ribs 112, 212." and insert -- ribs 112, 218. --, therefor.

In Column 4, Lines 53-54, delete "rib 112, 212 via" and insert -- rib 112, 218 via --, therefor.

In Column 4, Line 56, delete "rib 112, 212 and" and insert -- rib 112, 218 and --, therefor.

In Column 4, Line 57, delete "rib 112, 212 so" and insert -- rib 112, 218 so --, therefor.

In Column 4, Lines 57-58, delete "rib 112, 212 between" and insert -- rib 112, 218 between --, therefor.

Signed and Sealed this
Seventeenth Day of April, 2018

Andrei Iancu
*Director of the United States Patent and Trademark Office*